[54] S-(AMIDOCARBONYL)-METHYL-O-ALKYL-MONOTHIOPHOSPHORIC ACID ESTER AMIDES

[75] Inventors: Claus Stölzer, Wuppertal-Vohwinkel; Ingeborg Hammann, Cologne; Günter Unterstenhöfer, Opladen, all of Germany

[73] Assignee: Bayer Aktiengesellschaft, Leverkusen, Germany

[22] Filed: Mar. 24, 1975

[21] Appl. No.: 561,589

Related U.S. Application Data

[62] Division of Ser. No. 385,001, Aug. 2, 1973, Pat. No. 3,907,938.

[30] Foreign Application Priority Data

Aug. 16, 1972 Germany............................ 2240032

[52] U.S. Cl. .................. 424/200; 260/247.1 B; 260/293.85; 260/306.7 E; 260/309.6; 260/310 D
[51] Int. Cl.² ........................................ C07D 295/10
[58] Field of Search ................ 260/247.1 B, 293.85, 260/306.7, 309.6, 310 D; 424/200

[56] References Cited
UNITED STATES PATENTS

| | | | |
|---|---|---|---|
| 3,019,250 | 1/1962 | Kayser et al. ....................... | 260/943 |
| 3,758,644 | 9/1973 | Stolzer ................................ | 260/943 |
| 3,787,535 | 1/1974 | Stolzer ................................ | 260/943 |

OTHER PUBLICATIONS
Chemical Abstracts, 55:15418b (1961).
Chemical Abstracts, 64:19426e (1966).

*Primary Examiner*—Lorraine A. Weinberger
*Assistant Examiner*—Michael Shippen
*Attorney, Agent, or Firm*—Burgess, Dinklage & Sprung

[57] ABSTRACT

S-(amidocarbonyl)-methyl-O-alkyl monothiophosphoric acid ester amides of the formula

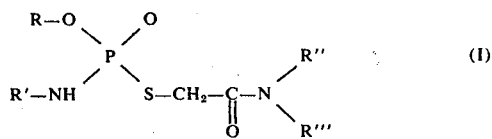

in which
R and R' each independently is alkyl of 1 to 6 carbon atoms,
R" is alkyl or alkenyl of 1 to 6 carbon atoms optionally carrying at least one chlorine, $C_1$–$C_6$ alkoxy, $C_1$–$C_6$ alkylmercapto or nitrile radical,
R''' is hydrogen or acyl, with the proviso that R''' is not hydrogen if R" is unsubstituted alkyl, or
R" and R''' conjointly with the nitrogen atom to which they are attached form a heterocyclic ring, which possess insecticidal and acaricidal properties.

7 Claims, No Drawings

S-(AMIDOCARBONYL)-METHYL-O-ALKYL-MONOTHIOPHOSPHORIC ACID ESTER AMIDES

This is a division, of application Ser. No. 385,001, filed Aug. 2, 1973, now U.S. Pat. No. 3,907,938.

The present invention relates to and has for its objects the provision of particular new S-(amidocarbonyl)-methyl-O-alkyl-monothiophosphoric acid ester amides, which possess insecticidal or acaricidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specification DAS 1,135,905 and U.S. Pat. No. 3,019,250 that the reaction products of O-alkyl-N-monoalkylamido-monothiophosphoric acid salts with substituted halogenomethyl compounds are distinguished by an insecticidal and acaricidal action.

The present invention provides, as new compounds, the S-(amidocarbonyl)-methyl-monothiophosphoric acid ester amides of the general formula

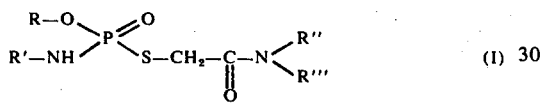

in which
R and R' each independently is alkyl of 1 to 6 carbon atoms,
R'' is alkyl or alkenyl of 1 to 6 carbon atoms optionally carrying at least one chlorine, $C_1$–$C_6$ alkoxy, $C_1$–$C_6$ alkylmercapto or nitrile radical,
R''' is hydrogen or acyl with the proviso that R''' is not hydrogen if R'' is unsubstituted alkyl, or
R'' and R''' conjointly with the nitrogen atom to which they are attached form a heterocyclic ring.

Surprisingly, the S-(amidocarbonyl)-methyl-monothiophosphoric acid ester amides of the formula (I) possess a substantially better insecticidal and acaricidal action than the known S-(amidocarbonyl)-methyl-monothio- and -dithiophosphoric acid O,O-dialkyl esters, which in respect of both structure and type of activity are the nearest comparable compounds and also the best-known commercially available products of this class of substance. The compounds according to the invention thus represent an enrichment of the art.

Preferably, R and R' are each straight-chain or branched lower alkyl with 1 to 4 carbon atoms (namely methyl, ethyl, iso- or n-propyl or n-, iso-, sec.- or tert.-butyl); R'' is lower alkyl with 1 to 4 carbon atoms which may be carrying one or more substituents selected from chlorine, $C_1$–$C_6$ alkoxy, $C_1$–$C_6$ alkylmercapto and nitrile, or is allyl; R''' is hydrogen or an acyl radical such as formyl, lower alkanoyl, benzoyl, carbo-lower alkoxy or carbophenoxy, especially formyl, acetyl, propionyl, butyryl, isobutyryl or benzoyl; and R'' and R''', when forming a heterocyclic ring, are piperidino, morpholino, thiazolino or diazolino.

The present invention also provides a process for the production of an S-(amidocarbonyl)-methyl-monothio-phosphoric acid ester amide of the formula (I) in which an O-alkyl-N-monoalkylamido-monothiophosphoric acid salt of the general formula

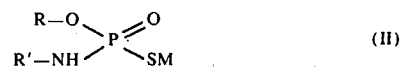

is reacted with a halogenoacetic acid amide of the general formula

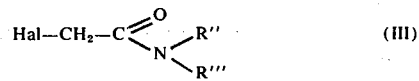

in which formulas
R, R', R'' and R''' have the above-mentioned meanings, Hal is halogen, preferably bromine or chlorine, and
M is an alkali metal equivalent, alkaline earth metal equivalent or optionally alkyl-substituted ammonium equivalent.

If the sodium salt of O-ethyl-N-monoisopropylamidomonothiophosphoric acid and chloroacetic acid morpholide are used as starting materials, the course of the reaction can be represented by the following equation:

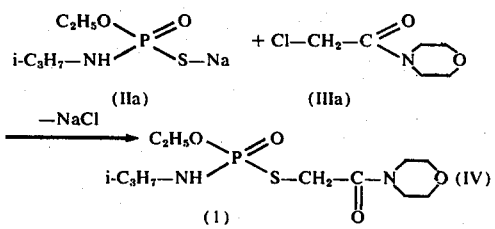

The following may be mentioned as examples of O-alkyl-N-monoalkylamidomothiophosphoric acid salts of the formula (II): the alkali metal salts, alkaline earth metal salts and optionally alkyl-substituted ammonium salts of O-methyl-N-methyl, O-methyl-N-propyl-, O-methyl-N-isopropyl-, O-ethyl-N-methyl-, O-ethyl-N-ethyl-, O-ethyl-N-isopropyl- and O-butyl-N-ethylamido-monothiophosphoric acids.

These salts and the halogenoacetic acid derivatives (III) are known and can be produced according to customary methods.

The preparative process for the new compounds (I) is preferably carried out with the conjoint use of a suitable solvent or diluent. Practically all inert organic solvents can be used for this purpose, especially aliphatic and aromatic, optionally chlorinated hydrocarbons, such as benzene, toluene, xylenes, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; nitriles, such as acetonitrile and propionitrile; and alcohols, for example methanol, ethanol and isopropanol. Water is also suitable as the solvent in certain cases.

The reaction temperature can be varied within a fairly wide range. In general the reaction is carried out at from 0° to 120°C, preferably at from 15° to 60°C.

The reaction is generally carried out under normal pressure.

To carry out the process, the starting materials are in most cases employed in equimolar amounts. An excess of one or other reaction component results in no substantial advantages. The reaction is preferably carried out in the presence of one of the above-mentioned solvents, at the indicated temperatures, and the reaction mixture is worked up in the usual manner after stirring for several hours.

The substances according to the invention are in most cases obtained in the form of colorless to slightly colored viscous water-soluble oils or crystals which, in general, cannot be distilled without decomposition but can be freed of the last volatile constituents by so-called "slight distillation", that is to say prolonged heating under reduced pressure to moderately elevated temperatures, and can be purified in this way. They are characterized, above all, by the refractive index and, in the case of the solid compounds, by the melting point.

As has already been mentioned, the new S-(amidocarbonyl)-methyl-monothiophosphoric acid ester amides are distinguished by an outstanding insecticidal and acaricidal activity against plant pests and pests harmful to health. They possess a good action against both sucking and biting insects and against mites (Acarina). At the same time they display only a slight phytotoxicity. For these reasons the compounds according to the invention may be successfully employed as pesticides in plant protection and in the hygiene field.

To the sucking insects there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (Triatoma infestans) and, further, cicadas, such as *Euscelis bilobatus* and *Nephotettix bipunctatus*.

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (Euproctis chrysorrhoea and tent caterpillar (*Malacosoma neustria*); further, the cabbage moth (*Mamestra brassicae*) and the cutworm (*Agrotis segetum*), the large white butterfly (Pieris brassicae), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*).

Also to be classed with the biting insects are beetles (Coleoptera), for example the granary weevil (*Sitophilus granarius* = *Calandra granaria*), the Colorado beetle (*Leptinotarsa decemlineata*), the dock beetle (Gastrophysa viridula), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (Stegobium paniceum), the yellow mealworm (*Tenebrio molitor*) and the sawtoothed grain beetle (*Oryzaephilus surinamensis*), and also species living in the soil, for example wireworms (Agriotes spec.) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyparobia maderae*), oriental cockroach (*Blatta orientalis*), the giant cockroach (Blaberus giganteus) and the black giant cockroach (*Blaberus fuscus*) as well as *Henschoutedenia flexivitta*; further Orthoptera, for example the house cricket (*Acheta domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stemoxys calcitrans*); further, gnats, for example mosquitoes such as the yellow fever mosquito (*Aedes aegypti*), the northern house mosquito (Culex pipiens) and the malaria mosquito (Anopheles stephensi).

With the mites (Acari) there are classed, in particular, the spider mites (Tetranychidae) such as the twospotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*tarsonemus pallidus*); finally, ticks, such as the relapsing fever tick (*ornithodorus moubata*).

When applied against pests harmful to health and pests of stored products, particularly flies and mosquitoes, the active compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alimina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides or rodenticides, fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

Example 1

Phaedon test (systemic long-term action)
Solvent: 3 parts by weight of acetone
Emulsifier: 1 part by weight of alkylaryl polyglycol ether To produce an appropriate preparation of active compound, 1 part by weight of active compound was mixed with the indicated amount of solvent which contained the indicated amount of emulsifier and the concentrate was diluted with water to the desired concentration of 0.025% of active compound.

Cabbage plants (*Brassica oleracea*) were watered with 50 ml portions of the active-compound preparation in such a way that the active-compound preparation entered the soil without wetting the leaves of the cabbage plants. The active compound was taken up by the cabbage plants from the soil and thus reached the leaves. 12.5 mg of active compound were used per 100 g of soil (weighed air-dry).

After the indicated times, the plants were infested with mustard beetle larvae (*Phaedon cochleariae*) and their destruction was in each case determined after 3 days as a percentage. 100% means that all of the larve were killed and 0% means that none of the larvae were killed.

The active compounds, active-compound concentrations, evaluation times and results can be seen from the following Table 1:

Cabbage plants (*Brassica oleracea*) were watered with 50 ml portions of the active-compound preparation in such a way that the active-compound prepara- Table 1

(Long-term action after watering: Phaedon cochleariae / Brassica oleracea)

| Active compound | mg of active compound per 100 g of soil (weighed air-dry) | % destruction after days: | | | | | | | |
|---|---|---|---|---|---|---|---|---|---|
| | | 10 | 17 | 20 | 24 | 27 | 31 | 34 | 41 | 48 |
| $(CH_3O)_2P(O)-S-CH_2-C(O)-NH-CH_3$ (known) (A) | 12.5 | 100 | 80 | 30 | | | | | | |
| $(C_2H_5O)(CH_3-NH)P(O)-S-CH_2-C(O)-NH-C(CH_3)_2-CN$ (12) | 12.5 | 100 | 100 | 100 | 70 | 50 | 50 | | | |
| $(C_2H_5O)(i-C_3H_7-NH)P(O)-S-CH_2-C(O)-NH-CH_2-OCH_3$ (8) | 12.5 | 100 | 100 | 100 | 100 | 100 | 100 | 100 | 100 | 100 |
| $(C_2H_5O)(i-C_3H_7-NH)P(O)-S-CH_2-C(O)-NH-CH_2-CH_2-OCH_3$ (3) | 12.5 | 100 | 100 | 100 | 100 | 100 | 100 | 20 | | |
| $(C_2H_5O)(i-C_3H_7-NH)P(O)-S-CH_2-C(O)-NH-C(CH_3)_2-CN$ (11) | 12.5 | 100 | 100 | 80 | 70 | 50 | 60 | | | |
| $(C_2H_5O)(i-C_3H_7-NH)P(O)-S-CH_2-C(O)-N(CH_3)(CHO)$ (4) | 12.5 | 100 | 100 | 100 | 100 | 90 | 60 | 40 | | |

Example 2

Myzus test (systemic long-term action)
Solvent: 3 parts by weight of acetone
Emulsifier: 1 part by weight of alkylaryl polyglycol ether To produce an appropriate preparation of active compound, 1 part by weight of active compound was mixed with the indicated amount of solvent which contained the indicated amount of emulsifier and the concentrate was diluted with water to the desired concentration of 0.025% active compound.

tion entered the soil without wetting the leaves of the cabbage plants. The active compound was taken up by the cabbage plants from the soil and thus reached the leaves. 12.5 mg of active compound were used per 100 g of soil (weighed air-dry).

After the indicated times, the plants were infested with aphids (*Myzus persicae*) and their destruction was in each case determined after 3 days as a percentage. 100% means that all the aphids were killed and 0% means that none of the aphids were killed.

The active compounds, active-compound concentrations, evaluation times and results can be seen from the following Table 2:

Table 2

(Long-term action after watering: Myzus persicae / Brassica oleracea)

| Active compound | mg of active compound per 100 g of soil (weighed air-dry) | % destruction after days: | | | | | | | |
|---|---|---|---|---|---|---|---|---|---|
| | | 17 | 20 | 24 | 31 | 38 | 41 | 45 | 48 | 52 |
| $(CH_3O)_2P(O)-S-CH_2-C(O)-NH-CH_3$ (known) (A) | 12.5 | 100 | 80 | 0 | | | | | | |
| $(CH_3O)_2P(S)-S-CH_2-C(O)-NH-CH_3$ (known) (B) | 12.5 | 100 | 100 | 100 | 100 | 75 | 50 | | | |
| $(C_2H_5O)(CH_3-NH)P(O)-S-CH_2-C(O)-NH-CH_2-OCH_3$ (6) | 12.5 | 100 | 100 | 100 | 100 | 100 | 100 | 100 | 50 | 50 |
| $(C_2H_5O)(CH_3-NH)P(O)-S-CH_2-C(O)-NH-CH_2-CH_2-OCH_3$ (5) | 12.5 | 100 | 100 | 100 | 100 | 100 | 100 | 100 | 100 | 100 |

Table 2-continued (Long-term action after watering: Myzus persicae / Brassica oleracea)

| Active compound | mg of active compound per 100 g of soil (weighed air-dry) | % destruction after days: | | | | | | | |
|---|---|---|---|---|---|---|---|---|---|
| | | 17 | 20 | 24 | 31 | 38 | 41 | 45 | 48 | 52 |
| (12) $C_2H_5O$–P(=O)(–NHCH_3)–S–CH_2–C(=O)–NH–C(CH_3)_2–CN | 12.5 | 100 | 100 | 100 | 100 | 100 | 100 | 100 | 100 | 100 |
| (10) $C_2H_5O$–P(=O)(–NHCH_3)–S–CH_2–C(=O)–N(CH_3)–CHO | 12.5 | 100 | 100 | 100 | 100 | 100 | 100 | 100 | 100 | 100 |
| (9) $C_2H_5O$–P(=O)(–NHCH_3)–S–CH_2–C(=O)–N(CH_3)–C(=O)–OC_2H_5 | 12.5 | 100 | 100 | 100 | 100 | 100 | 100 | 100 | 100 | 100 |
| (8) $C_2H_5O$–P(=O)(–NH-i-C_3H_7)–S–CH_2–C(=O)–NH–CH_2–OCH_3 | 12.5 | 100 | 100 | 100 | 100 | 100 | 100 | 100 | 100 | 100 |
| (11) $C_2H_5O$–P(=O)(–NH-i-C_3H_7)–S–CH_2–C(=O)–NH–C(CH_3)_2–CN | 12.5 | 100 | 100 | 100 | 100 | 100 | 100 | 0 | | |
| (4) $C_2H_5O$–P(=O)(–NH-i-C_3H_7)–S–CH_2–C(=O)–N(CH_3)–CHO | 12.5 | 100 | 100 | 100 | 100 | 100 | 100 | 100 | 100 | 100 |
| (14) $C_2H_5O$–P(=O)(–NH-i-C_3H_7)–S–CH_2–C(=O)–N(CH_3)–C(=O)–CH(CH_3)_2 | 12.5 | 100 | 100 | 100 | 100 | 100 | 100 | 100 | 100 | 100 |

Example 3

Phorodon test (contact action/resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Hop plants (*Humulus lupulus*), which were heavily infested with the hop-damson aphid (*Phorodon humuli*/resistant), were sprayed with the preparation of the active compound until dripping wet.

After the specified periods of time, the degree of destruction was determined as a percentage. 100% means that all the aphids were killed whereas 0% means that none of the aphids were killed.

The active compounds, the concentrations of the active compounds, the evaluation times and the results can be seen from the following Table 3:

Table 3

| Active compound | (Phorodon humuli / resistant) Active compound concentration in % | Degree of destruction in % after 1 day |
|---|---|---|
| (A) (known) $CH_3O$–P(=O)(–OCH_3)–S–CH_2–C(=O)–NH–CH_3 | 0.1<br>0.02 | 50<br>30 |
| (12) $C_2H_5O$–P(=O)(–NH–CH_3)–S–CH_2–C(=O)–NH–C(CH_3)_2–CN | 0.1<br>0.02<br>0.004 | 100<br>100<br>100 |

Table 3-continued

| Active compound | (Phorodon humuli / resistant) Active compound concentration in % | Degree of destruction in % after 1 day |
| --- | --- | --- |
| $\begin{array}{c}C_2H_5O\\ \phantom{xx}\diagdown P \diagup\!\!=\!\!O\\ CH_3\text{—}NH \diagup \phantom{xx}\diagdown S\text{—}CH_2\text{—}\underset{\underset{O}{\|}}{C}\text{—}N\!\!<\!\!\!\begin{array}{c}\phantom{x}\\ \phantom{x}\end{array}\!\!\!O \end{array}$ (7) | 0.1<br>0.02 | 100<br>98 |
| $\begin{array}{c}C_2H_5O\\ \phantom{xx}\diagdown P \diagup\!\!=\!\!O\\ i\text{-}C_3H_7\text{—}NH \diagup \phantom{xx}\diagdown S\text{—}CH_2\text{—}\underset{\underset{O}{\|}}{C}\text{—}N\!\!<\!\!\!\begin{array}{c}i\text{-}C_3H_7\\ \underset{\underset{O}{\|}}{C}\text{—}CH_3\end{array} \end{array}$ (13) | 0.1<br>0.02<br>0.004 | 100<br>100<br>60 |

Example 4

Myzus test (contact action)/resistant
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which had been heavily infested with peach aphids (*Myzus persicae*/resistant), were sprayed with the preparation of the active compound until dripping wet.

After the specified periods of time, the degree of destruction was determined as a percentage: 100% means that all the aphids were killed, whereas 0% means that none of the aphids were killed.

The active compounds, the concentrations of the active compounds, the evaluation times and the results can be seen from the following Table 4:

Table 4

| Active compound | (Myzus persicae / resistant) Active compound concentration in % | Degree of destruction in % after 1 day |
| --- | --- | --- |
| $\begin{array}{c}CH_3O\\ \phantom{xx}\diagdown \underset{\underset{}{}}{P}\!\!<\!\!\!\!\begin{array}{c}O\\ \|\end{array}\!\!\!\!\text{—}S\text{—}CH_2\text{—}\underset{\underset{O}{\|}}{C}\text{—}NH\text{—}CH_3\\ CH_3O\end{array}$ (known) (A) | 0.1<br>0.02 | 50<br>20 |
| $\begin{array}{c}CH_3O\\ \phantom{xx}\diagdown \underset{\underset{}{}}{P}\!\!<\!\!\!\!\begin{array}{c}S\\ \|\end{array}\!\!\!\!\text{—}S\text{—}CH_2\text{—}\underset{\underset{O}{\|}}{C}\text{—}NH\text{—}CH_3\\ CH_3O\end{array}$ (known) (B) | 0.1<br>0.02 | 90<br>65 |
| $\begin{array}{c}C_2H_5O\\ \phantom{xx}\diagdown P \diagup\!\!=\!\!O\\ CH_3\text{—}NH \diagup \phantom{xx}\diagdown S\text{—}CH_2\text{—}\underset{\underset{O}{\|}}{C}\text{—}N\!\!<\!\!\!\begin{array}{c}\phantom{x}\\ \phantom{x}\end{array}\!\!\!O\end{array}$ (7) | 0.1<br>0.02<br>0.004 | 100<br>100<br>50 |
| $\begin{array}{c}C_2H_5O\\ \phantom{xx}\diagdown P \diagup\!\!=\!\!O\\ i\text{-}C_3H_7\text{—}NH \diagup \phantom{xx}\diagdown S\text{—}CH_2\text{—}\underset{\underset{O}{\|}}{C}\text{—}N\!\!<\!\!\!\begin{array}{c}i\text{-}C_3H_7\\ \underset{\underset{O}{\|}}{C}\text{—}CH_3\end{array}\end{array}$ (13) | 0.1<br>0.02 | 100<br>90 |

Example 5

Rhopalosiphum test (systemic action)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Oat plants (*Avena sativa*), which had been strongly infested with the bird cherry aphid (*Rhopalosiphum padi*), were watered with the preparation of the active compound so that the preparation penetrated into the soil without wetting the leaves of the oat plants. The active compound was taken up by the oat plants from the soil and thus reached the infested leaves.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following Table 5:

Table 5

| Active compound | (Rhopalosiphum test / systemic action) Active compound concentration in % | Degree of destruction in % after 4 days |
| --- | --- | --- |
| $\begin{array}{c}CH_3O\\ \phantom{xx}\diagdown \underset{\underset{}{}}{P}\!\!<\!\!\!\!\begin{array}{c}O\\ \|\end{array}\!\!\!\!\text{—}S\text{—}CH_2\text{—}\underset{\underset{O}{\|}}{C}\text{—}NH\text{—}CH_3\\ CH_3O\end{array}$ (known) (A) | 0.1<br>0.01<br>0.001<br>0.0001 | 100<br>100<br>100<br>0 |

Table 5-continued (Rhopalosiphum test / systemic action)

| Active compound | Active compound concentration in % | Degree of destruction in % after 4 days |
|---|---|---|
| $C_2H_5O$\P(=O)/$CH_3-NH$\S-$CH_2$-C(=O)-N⟨O⟩ (7) | 0.1<br>0.01<br>0.001<br>0.0001 | 100<br>100<br>100<br>99 | spotted spider mite (*Tetranychus urticae*) in all stages of development.

After the specified periods of time, the effectiveness of the preparation of active compound was determined by counting the dead mites. The degree of destruction thus obtained was expressed as a percentage: 100% means that all the spider mites were killed whereas 0% means that none of the spider mites were killed.

The active compounds, the concentrations of the active compounds, the evaluation times and the results can be seen from the following Table 6:

Table 6

(Tetranychus test / resistant)

| Active compound | Active compound concentration in % | Degree of destruction in % after 2 days |
|---|---|---|
| $CH_3O$\P(=S)/$CH_3O$\S-$CH_2$-C(=O)-NH-$CH_3$ (known) (B) | 0.1<br>0.01 | 95<br>0 |
| $C_2H_5O$\P(=O)/i-$C_3H_7$-NH\S-$CH_2$-C(=O)-NH-$CH_2$-$OCH_3$ (8) | 0.1<br>0.01 | 100<br>70 |
| $C_2H_5O$\P(=O)/i-$C_3H_7$-NH\S-$CH_2$-C(=O)-NH-C($CH_3$)($CN$)$CH_3$ (11) | 0.1<br>0.01 | 98<br>50 |
| $C_2H_5O$\P(=O)/i-$C_3H_7$-NH\S-$CH_2$-C(=O)-N($CH_3$)-C(=O)-CH($CH_3$)$_2$ (14) | 0.1<br>0.01 | 100<br>90 |
| $C_2H_5O$\P(=O)/i-$C_3H_7$-NH\S-$CH_2$-C(=O)-N($CH_3$)-C(=O)-O-$C_2H_5$ (2) | 0.1<br>0.01 | 98<br>30 |
| $C_2H_5O$\P(=O)/i-$C_3H_7$-NH\S-$CH_2$-C(=O)-N(i-$C_3H_7$)-C(=O)-$CH_3$ (13) | 0.1<br>0.01 | 100<br>99 |

Example 6

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages The process of this invention is illustrated in the following preparative Example.

EXAMPLE 7

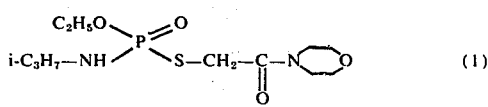

(1)

32.7 (0.20 mole) of chloroacetic acid morpholide in 50 ml of acetonitrile were added dropwise at room temperature to a solution of 62.0 g (0.28 mole) of the sodium salt of O-ethyl-N-monoisopropylamido-monothiophosphoric acid in 300 ml of acetonitrile. The reaction was slightly exothermic. The mixture was stirred overnight at 40° to 60°C, and the inorganic salts which had separated out were filtered off. The solvent was removed, the residue was taken up in dichloromethane, the solution was twice washed with a little water, and the organic phase was dried over sodium sulfate and filtered. The filtrate was concentrated and S-(morpholidocarbonyl)-methyl-O-ethyl-N-monoisopropyl-monothiophosphoric acid ester amide was obtained as a yellow, viscous, water-soluble oil of refractive index $n_D^{23}$ of 1.5153. The yield was 40.3 g (64.8% of theory).

The following compounds were obtained by methods analogous to that described above.

| Formula | Melting point/ refractive index |
|---|---|
| (2) $C_2H_5O\!-\!\!\underset{i\text{-}C_3H_7\!-\!NH}{\overset{}{P}}\!\!\overset{O}{=}\!\!\underset{S\!-\!CH_2\!-\!\underset{\underset{O}{\parallel}}{C}\!-\!N(\!\!\!\!\!\!\!\underset{\underset{O}{\parallel}}{\overset{CH_3}{}}\!\!\!)\!-\!C\!-\!O\!-\!C_2H_5}{}$ | $n_D^{23}$ 1.4818 |
| (3) $C_2H_5O\!-\!P(\!=\!O)(\!NH\text{-}i\text{-}C_3H_7)\!-\!S\!-\!CH_2\!-\!C(\!=\!O)\!-\!NH\!-\!CH_2\!-\!CH_2\!-\!OCH_3$ | $n_D^{23}$ 1.4958 |
| (4) $C_2H_5O\!-\!P(\!=\!O)(\!NH\text{-}i\text{-}C_3H_7)\!-\!S\!-\!CH_2\!-\!C(\!=\!O)\!-\!N(CH_3)(CHO)$ | M.p. 51 to 53°C |
| (5) $C_2H_5O\!-\!P(\!=\!O)(\!NH\!-\!CH_3)\!-\!S\!-\!CH_2\!-\!C(\!=\!O)\!-\!NH\!-\!CH_2\!-\!CH_2\!-\!OCH_3$ | $n_D^{22}$ 1.5223 |
| (6) $C_2H_5O\!-\!P(\!=\!O)(\!NH\!-\!CH_3)\!-\!S\!-\!CH_2\!-\!C(\!=\!O)\!-\!NH\!-\!CH_2\!-\!OCH_3$ | $n_D^{22}$ 1.5020 |
| (7) $C_2H_5O\!-\!P(\!=\!O)(\!NH\!-\!CH_3)\!-\!S\!-\!CH_2\!-\!C(\!=\!O)\!-\!N(\text{morpholino})$ | $n_D^{20}$ 1.5271 |
| (8) $C_2H_5O\!-\!P(\!=\!O)(\!NH\text{-}i\text{-}C_3H_7)\!-\!S\!-\!CH_2\!-\!C(\!=\!O)\!-\!NH\!-\!CH_2\!-\!OCH_3$ | M.p. 47°C |
| (9) $C_2H_5O\!-\!P(\!=\!O)(\!NH\!-\!CH_3)\!-\!S\!-\!CH_2\!-\!C(\!=\!O)\!-\!N(CH_3)\!-\!C(\!=\!O)\!-\!OC_2H_5$ | $n_D^{21}$ 1.4959 |
| (10) $C_2H_5O\!-\!P(\!=\!O)(\!NH\!-\!CH_3)\!-\!S\!-\!CH_2\!-\!C(\!=\!O)\!-\!N(CH_3)(CHO)$ | $n_D^{20}$ 1.5168 |
| (11) $C_2H_5O\!-\!P(\!=\!O)(\!NH\text{-}i\text{-}C_3H_7)\!-\!S\!-\!CH_2\!-\!C(\!=\!O)\!-\!NH\!-\!C(CH_3)_2(CN)$ | $n_D^{25}$ 1.4940 |
| (12) $C_2H_5O\!-\!P(\!=\!O)(\!NH\!-\!CH_3)\!-\!S\!-\!CH_2\!-\!C(\!=\!O)\!-\!NH\!-\!C(CH_3)_2(CN)$ | $n_D^{25}$ 1.5025 |
| (13) $C_2H_5O\!-\!P(\!=\!O)(\!NH\text{-}i\text{-}C_3H_7)\!-\!S\!-\!CH_2\!-\!C(\!=\!O)\!-\!N(i\text{-}C_3H_7)\!-\!C(\!=\!O)\!-\!CH_3$ | $n_D^{20}$ 1.4945 |
| (14) $C_2H_5O\!-\!P(\!=\!O)(\!NH\text{-}i\text{-}C_3H_7)\!-\!S\!-\!CH_2\!-\!C(\!=\!O)\!-\!N(CH_3)\!-\!C(\!=\!O)\!-\!CH(CH_3)_2$ | $n_D^{20}$ 1.4929 |

-continued

| Formula | Melting point/refractive index |
|---|---|
| (15) $C_2H_5O\diagdown P\diagup O$ $CH_3-NH\diagup\phantom{P}\diagdown S-CH_2-\underset{\underset{O}{\|}}{C}-NH-CH_2-CH=CH_2$ | $n_D^{20}$ 1.5170 |
| (16) $C_2H_5O\diagdown P\diagup O$ $i\text{-}C_3H_7-NH\diagup\phantom{P}\diagdown S-CH_2-\underset{\underset{O}{\|}}{C}-NH-CH_2-CH=CH_2$ | $n_D^{20}$ 1.5031 |
| (17) $C_2H_5O\diagdown P\diagup O$ $i\text{-}C_3H_7-NH\diagup\phantom{P}\diagdown S-CH_2-\underset{\underset{O}{\|}}{C}-NH-CH_2-CH_2-Cl$ | $n_D^{20}$ 1.5080 |
| (18) $C_2H_5O\diagdown P\diagup O$ $i\text{-}C_3H_7-NH\diagup\phantom{P}\diagdown S-CH_2-\underset{\underset{O}{\|}}{C}-NH-CH_2-CH_2-SCH_3$ | M.p. 57–59°C |
| (19) $C_2H_5O\diagdown P\diagup O$ $CH_3-NH\diagup\phantom{P}\diagdown S-CH_2-\underset{\underset{O}{\|}}{C}-NH-CH_2-CH_2-Cl$ | $n_D^{20}$ 1.5192 |
| (20) $C_2H_5O\diagdown P\diagup O$ $CH_3-NH\diagup\phantom{P}\diagdown S-CH_2-\underset{\underset{O}{\|}}{C}-NH-CH_2-CH_2-SCH_3$ | $n_D^{20}$ 1.5365 |

It will be appreciated that the instant specification and examples are set forth by way of illustration and not limitation, and that various modifications and changes may be made without departing from the spirit and scope of the present invention.

What is claimed is:

1. An S-(amidocarbonyl)-methylmonothiophosphoric acid ester amide of the formula

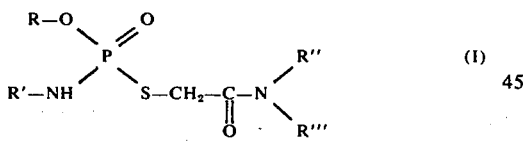

in which
R and R' each independently is alkyl of 1 to 6 carbon atoms, and
R'' and R''' conjointly with the nitrogen atom to which they are attached form a piperidino, morpholino, thiazolino or diazolino ring.

2. A compound according to claim 1, in which R and R' each independently is alkyl of 1 to 4 carbon atoms.

3. The compound according to claim 1, wherein such compound is S-(morpholidocarbonyl)-methyl-O-ethyl-N-monomethylmonothiophosphoric acid ester amide of the formula

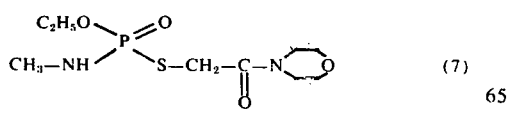

4. A compound according to claim 1, wherein such compound is S-(morpholidocarbonyl)-methyl-O-ethyl-N-monoisopropyl-monothiophosphoric acid ester amide of the formula

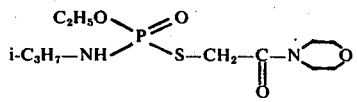

5. An insecticidal or acaricidal composition comprising an insecticidally or acaricidally effective amount of a compound according to claim 1 in admixture with a diluent.

6. A method of combating insects or acarids which comprises applying to the insects or acarids, or a habitat thereof, an insecticidally or acaricidally effective amount of a compound according to claim 1.

7. The method according to claim 6 in which said compound is:
S-(morpholidocarbonyl)-methyl-O-ethyl-N-monomethylmonothiophosphoric acid ester amide and,
S-(merpholidocarbonyl)-methyl-O-ethyl-N-monoisopropyl-monothiophosphoric acid ester amide.